United States Patent [19]
Goodman et al.

[11] Patent Number: 5,888,475
[45] Date of Patent: Mar. 30, 1999

[54] LABELED COCAINE ANALOGS

[75] Inventors: Mark M. Goodman, Atlanta; Bing Zhi Shi, Tucker; Robert N. Keil, Atlanta, all of Ga.

[73] Assignee: Emory University, Atlanta, Ga.

[21] Appl. No.: 948,791

[22] Filed: Oct. 10, 1997

Related U.S. Application Data

[62] Continuation of PCT/US96/13471, Aug. 12, 1996 which is a division of Ser. No. 512,516, Aug. 17, 1995.

[51] Int. Cl.[6] .......................... A61K 51/04; A61K 31/46; C07D 451/02
[52] U.S. Cl. ...................... 424/1.85; 424/1.89; 546/132; 206/223
[58] Field of Search ................................... 424/185, 189; 206/223; 546/132

[56] References Cited

U.S. PATENT DOCUMENTS

| | | | |
|---|---|---|---|
| 5,128,118 | 7/1992 | Carroll et al. | 424/1.85 |
| 5,310,912 | 5/1994 | Neumeyer et al. | 546/132 |
| 5,380,848 | 1/1995 | Kuhar et al. | 546/124 |

OTHER PUBLICATIONS

Gatley et al., (1994) "Studies with differentially labeled [$^{11}$C]cocaine, [$^{11}$C]norocaine, [$^{11}$C]benzoylecgonine, and [$^{11}$C]—and 4'-[$^{18}$F]fluorococaine to probe the extent to which [$^{11}$C]cocaine metabolites contribute to PET images of the baboon brain," *J. Neurochem.* 62:1154–1162.

Clark et al. (1973) "Compounds affecting the central nervous system. 4.3β–phenyltropane–2–carboxylic esters and analogs," *J. Med. Chem.* 16:1260–1267.

Madras et al. (1989) "Cocaine receptors labeled by [$^{3}$H] 2β–carbomethoxy–3β–(4–fluorophenyl)tropane," *Mol. Pharmacol.* 36:518–524.

Davies et al. (1994) "Synthesis of 2β–acyl–3βaryl–8–azabicyclo[3.2.1]octanes and their binding affinities at dopamine and serotonin transport sites in rat striatum and frontal cortex," *J. Med. Chem.* 37: 1262–1268.

Milius et al. (1991) "Synthesis of receptor binding of n–substituted tropane derivatives. High–affinity ligands for the cocaine receptor," *J. Med. Chem.* 34:1728–1731.

Madras et al. (1990) "N–modified fluorophenyltropane analogs with high affinity for cocaine receptors," *Pharmacology Biochemistry and Behavior* 35:949–953.

Dannals et al. (1992) "Synthesis of radiotracer for studying dopamine uptake sites in vivo using PET: 2β–carbomethpoxy–3β–(4–fluorophenyl)–[N–$^{11}$C–methyl] tropane ([$^{11}$C]CFT or [$^{11}$C]WIN–35,428)," *J. Labelled Compounds and Radiopharmaceuticals* 33:147–152.

Calne et al. 91985) "Positron emission tomography after MPTP: observations relating to the cause of Parkinson's disease," *Nature* 317:246–248.

Goodman et al. (1995) *J. Nucl. Med.* 36:38P, Abstract No. 150 (Proceedings of the 42nd Annual Meeting of the Society of Nuclear Medicine, Minneapolis, MN, Jun. 12–15.

Primary Examiner—Alan L. Rotman
Attorney, Agent, or Firm—Greenlee Winner & Sullivan

[57] ABSTRACT

Novel methods for positron emission tomography or single photon emission spectroscopy using tracer compounds having the structure:

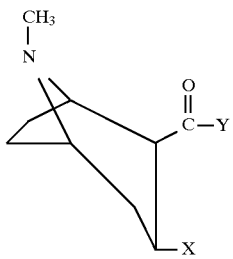

where
X in β configuration is
phenyl, naphthyl; 2,3 or 4-iodophenyl; 2,3 or 4-(trimethylsilyl)phenyl; 3,4,5 or 6-iodonaphthyl; 3,4,5 or 6-(trimethylsilyl)naphthyl; 2,3 or 4-(trialkylstannyl)phenyl; or 3,4,5 or 6-(trialkylstannyl)napthyl Y in β configuration is
2-fluoroethoxy, 3-fluoropropoxy, 4-fluorobutoxy, 2-fluorocyclopropoxy, 2 or 3-fluorocyclobutoxy, R,S 1'-fluoroisopropoxy, R 1'-fluoroisopropoxy, S 1'-fluoroisopropoxy, 1',3'-difluoroisopropoxy, R,S 1'-fluoroisobutoxy, R 1'-fluoroisobutoxy, S 1'-fluoroisobutoxy, R,S 4'-fluoroisobutoxy, R 4'-fluoroisobutoxy, S 4'-fluoroisobutoxy, or 1',1'-di (fluoromethyl)isobutoxy, The compounds bind dopamine transporter protein and can be labeled with $^{18}$F or $^{123}$I for imaging.

3 Claims, No Drawings

LABELED COCAINE ANALOGS

CROSS REFERENCE TO RELATED APPLICATIONS

This application is a continuation of PCT/US96/13471 filed Aug. 12, 1996, which is a division of U.S. Ser. No. 08/512,516 filed Aug. 17, 1995.

BACKGROUND OF THE INVENTION

The invention relates to certain substituted tropanes useful for positron emission tomography (PET) imaging and single photon emission (SPECT) imaging methods.

Analogs of cocaine (2β-carbomethoxy-3β-benzoxytropane) (Compound I) are useful in the study of brain function, in particular the dopamine transporter protein and the serotonin transporter protein. Such studies have yielded useful insights into the metabolism and mechanism of action regarding the psychoactivity and addictive properties of cocaine. In addition, fundamental insights have been learned about the physiology and biochemistry of the dopamine and serotonin transporters in normal and pathogenic conditions.

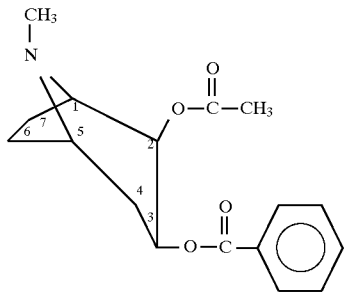

COMPOUND I

The ability of cocaine and certain analogs thereof to bind to localized receptors within the brain would make it possible, in principle, to utilize the compounds for in situ imaging of the receptors by PET, SPECT and similar imaging methods. PET imaging is accomplished with the aid of tracer compounds labeled with a positron-emitting isotope (Goodman, M. M. *Clinical Positron Emission Tomography*, Mosby Yearbook, 1992, K. F. Hubner et al., Chapter 14). For most biological materials, suitable isotopes are few. The carbon isotope, [$^{11}$C], has been used for PET, but its short half-life of 20.5 minutes limits its usefulness to compounds that can be synthesized and purified quickly, and to facilities that are proximate to a cyclotron where the precursor [$^{11}$C] starting material is generated. Other isotopes have even shorter half-lives. [$^{13}$N] has a half-life of 10 minutes and [·O] has an even shorter half-life of 2 minutes. The emissions of both are more energetic than those of [$^{11}$C]. Nevertheless, PET studies have been carried out with these isotopes (Hubner, K. F., in *Clinical Positron Emission Tomography*, Mosby Year Book, 1992, K. F. Hubner, et al., Chapter 2). A more useful isotope,[$^{18}$F], has a half-life of 110 minutes. This allows sufficient time for incorporation into a radio-labeled tracer, for purification and for administration into a human or animal subject. In addition, facilities more remote from a cyclotron, up to about a 200 mile radius, can make use of [$^{18}$F] labeled compounds. Disadvantages of [$^{18}$F] are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $^{18}$F-F. Reactions using $^{18}$F-F as starting material therefore yield products having only one half the radionuclide abundance of reactions utilizing K$^{18}$F as starting material. On the other hand, [$^{18}$F] can be prepared in curie quantities as fluoride ion for incorporation into a radiopharmaceutical compound in high specific activity, theoretically 1.7 Ci/nmol using carrier-free nucleophilic substitution reactions. The energy emission of [$^{18}$F] is 0.635 MeV, resulting in a relatively short, 2.4 mm average positron range in tissue, permitting high resolution PET images.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is [$^{123}$I], a γ-emitter with a 13.3 hour half life. Compounds labeled with [$^{123}$I] can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Use of [$^{18}$F] labeled compounds in PET has been limited to a few analog compounds. Most notably, [$^{18}$F]-fluorodeoxyglucose has been widely used in studies of glucose metabolism and localization of glucose uptake associated with brain activity. [$^{18}$F]-L-fluorodopa and other dopamine receptor analogs have also been used in mapping dopamine receptor distribution.

Various fluorinated cocaine analogs have been synthesized. Gatley et al., (1994) *J. Neurochem.* 62:1154–1162 reported synthesis of 4'-[$^{18}$F]fluorococaine (Compound II) by nucleophilic aromatic substitution from [$^{18}$F]fluoride and 4'-nitrococaine. A yield of 10–15% corrected for decay was reported. The yield was believed to be reduced by hydrolysis of both substrate and product under the basic reaction conditions. PET images acquired with $^{18}$F- or $^{11}$C-labeled 4'-fluorococaine were very similar to those acquired with [N-methyl-$^{11}$CH$_3$] cocaine.

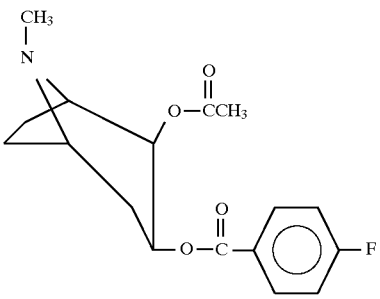

COMPOUND II

Compounds of the general class 3β-aryltropane-2β-carboxylates have been shown to be, in some cases, up to 500 times more potent than cocaine at binding the dopamine transporter. In particular, the 4'-fluorophenyl derivative (Compound III) has been widely employed and is commercially available. Trivial names for this compound are WIN 35,428 and CFT. (Clark et al., (1973) *J. Med. Chem.* 16:1260–1267; Madras et al., (1989) *Mol. Pharmacol.* 36:518–524). According to Gatley et al (1994) supra, no routes of synthesis were available to high specific activity [$^{18}$F-] labeled WIN 35,428 (III) since it lacks a functionality to activate a leaving group at the 4' position to nucleophilic displacement with [$^{18}$F]F$^-$. In addition, the iodo compound (2β-Carbomethoxy-3β-(4-iodophenyl)tropane, also called RTI-55 (Compound IV), has been synthesized (Davies et al., (1994) *J. Med. Chem.* 37: 1262–1268). The latter authors reported synthesis of a series of 2β-methyl ketone and -ethyl ketone compounds, replacing the ester linkage at the 2β position found in cocaine (I) and WIN 35,428 (III). Para fluorophenyl derivatives (such as Compound V) were synthesized by a copper-catalyzed addition reaction using a p-fluorophenyl magnesium bromide precursor. No isotopically labeled compounds of this type were reported. Binding of the compounds to dopamine transporter and serotonin receptor was observed, measured in vitro by competitive inhibition of [$^{125}$I]-RTI-55 (IV) binding in homogenates of rat brain striata.

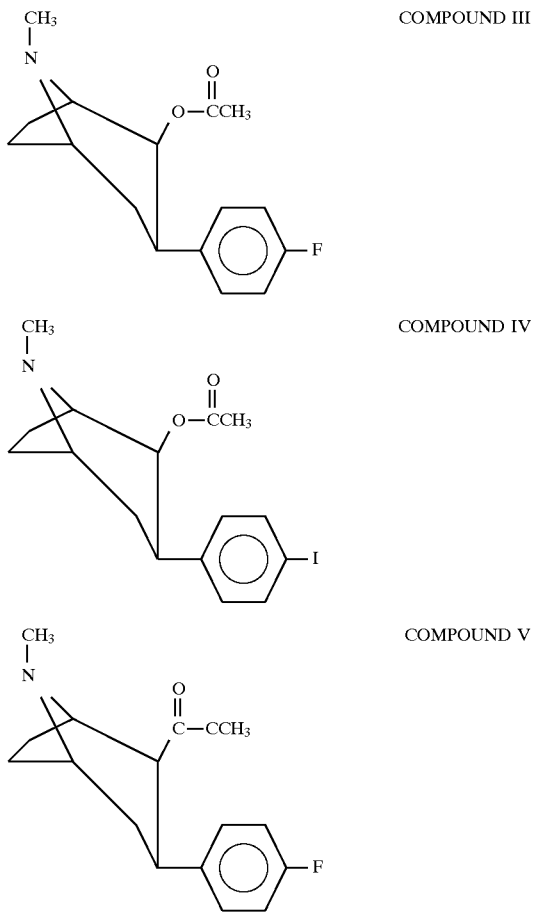

A series of N-substituted derivatives of WIN 35,428 (III) were reported by Milius et al., (1991) *J. Med. Chem.* 34: 1728–1731. Synthesis was based on WIN 35,428 (III) as starting material. The latter was itself synthesized by reaction of p-fluorophenylmagnesium bromide with anhydroecgonine methyl ester. Binding was observed in vitro, measured by competition with [$^3$H]-cocaine (I) in homogenates of monkey brain caudate putamen. None of the described derivatives was isotope labeled.

Madras et al., (1990) *Pharmacology Biochemistry and Behavior* 35:949–953 reported comparisons of three N-modified fluorophenyl analogs of WIN 35,428 (III), the N-allyl, N-propyl and the N-unsubstituted compound. All three analogs displaced specifically bound [$^3$H] cocaine (I) in vitro from caudate-putamen homogenates of monkey brain with affinities greater than that of cocaine. In vivo tests with monkeys confirmed cocaine-like interoceptive effects of the analogs. The analogs were synthesized as described by Milius (1991), supra. No synthesis of isotope-labeled analogs was reported.

Delalande, S. A., German OS 30 01 328, disclosed a series of nortropane derivatives having a variety of aromatic and heterocyclic N-substituents and a variety of aromatic and heterocyclic substituents in amide linkage at the 3 position of the tropane nucleus. Included in the N-substituents are fluoro-substituted aromatics, such as Compound VI, the synthesis of which employed a p-fluorobenzyl chloride intermediate. No synthesis using a fluorine isotope was reported.

Kuhar et al, U.S. Pat. No. 5,380,848, issued Jan. 10, 1995, disclosed nortropane analogs having a variety of N-substituents, various substituents at the 2-position and various aromatic substituents at the 3-position. Certain halogenated substituents were disclosed, both as alkyl halogens (specifically, 2-chloromethyl) and as halogen-substituted aromatic groups at the 3-position. Synthesis of 3β-(3'-Methyl-4'-fluorophenyl) tropane-2β-carboxylic acid methyl ester (Compound VII) was disclosed

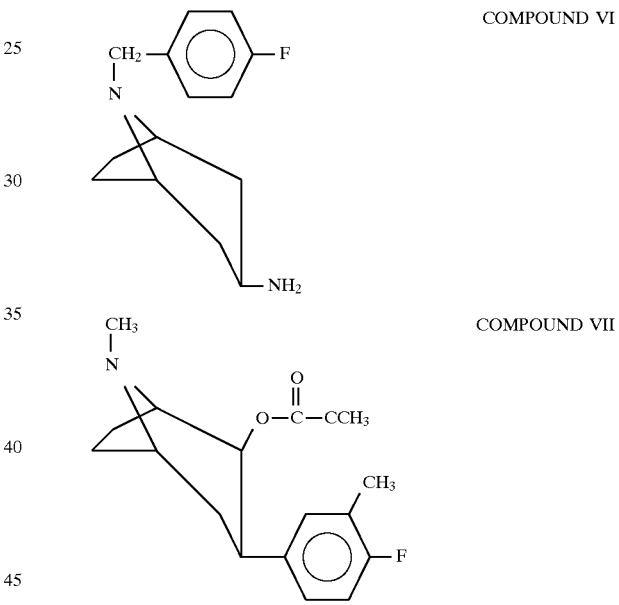

using 3-methyl-4-fluorophenylmagnesium bromide as the fluorinated starting material, with 29% yield of the stated product. Use of radiocarbon or radioiodine for tracer labeling was described generally, and use of [$^{11}$C] as label for PET imaging was discussed. Labeling with [$^{18}$F] was not disclosed. No isotopic synthesis was described. The ability of the disclosed compounds to displace [$^3$H]WIN 35,248 (III) in an in vitro assay using rat brain striata homogenates was compared.

Neumeyer et al, U.S. Pat. No. 5,310,912, issued may 10, 1994, disclosed N-substituted, 2-carboalkoxy-3-aryl nortropanes including N-substituted fluoroalkyl derivatives. 1-bromo-3-fluoropropane was reacted with the corresponding nortropane to generate 2β-carbomethoxy-3β-(-iodophenyl)-8-(3-fluoropropyl)-nortropane (Compound VIII). No binding or activity results were reported with regard to the product. No yield data for the synthesis of the final product or the 1-bromo-3-fluoropropane starting material were reported. Longer 2-substituted alkoxy derivatives, up to 6 carbons, were described. No fluoro-derivatives thereof were disclosed. The patent also disclosed the iodo-analog (IV) of WIN 35,428 (III), synthesized by direct iodination of 2β-carbomethoxy-3-β-phenyltropane. The compound, 2β-carbomethoxy-3β-(4'-iodophenyl)-tropane, was abbreviated β-CIT or alternatively RTI-55 (IV). Also, [$^{123}$I] label was introduced by converting the iodinated compound to the corresponding tributyl tin derivative followed by reaction with Na$^{123}$I resulting in a labeled compound having about 2000 Ci/mmol. β-CIT (IV) was shown to bind dopamine reuptake sites in tissue homogenates of primate striatum in competition with tritiated WIN 35,428 (III).

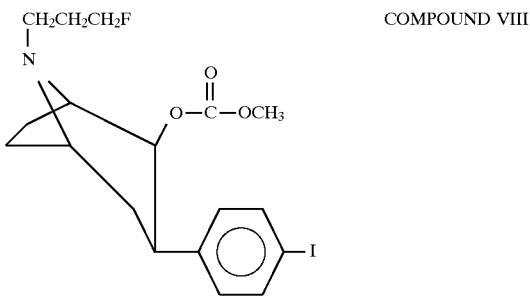

COMPOUND VIII

Dannals et al., (1992) *J. Labelled Compounds and Radiopharmaceuticals* 33: 147–152 disclosed [$^{11}$C] labeled WIN 35,428 (III) and method of synthesis thereof by N-methylation of the corresponding free base using $^{11}$CH$_3$I. The synthesis required about 21 minutes with a yield of 20.6% not corrected for decay. The labeled compound was intended for use in PET imaging of the dopamine uptake site. Although the compound also contains a fluorine, no synthesis of an [$^{18}$F]-labeled compound was reported.

Dopamine (4-(2-aminoethyl)-1,2-benzenediol) is a neurotransmitter in certain parts of the central nervous system (CNS). Neurons responsive to dopamine are termed dopaminergic. Dopamine is synthesized and released by presynaptic dopaminergic neurons and exerts its effects by binding at post-synaptic receptors. Following impulse transmission, dopamine in the synaptic gap is removed by binding to a dopamine transporter protein. The latter thus acts to regulate the amount of free dopamine in the synaptic gap and to prevent continuous excitation of the post-synaptic neurons.

Abnormalities in CNS dopaminergic neurotransmission have been implicated in movement disorders such as Parkinson's disease. This disorder has been shown to be caused by a significant decrease in the synthesis and transmission of dopamine as a result of degeneration of dopamine neurons in the substantia nigra and corpus striatum regions of the brain. Parkinson's disease has been characterized as a result of progressive loss of neurons in the substantia nigra in which age-related attrition is exacerbated or accelerated by an environmental insult of some sort (Calne et al (1985) *Nature* 317:246–248). Although drug therapy is of some value, its effectiveness diminishes as the disease progresses. Early diagnosis is therefore of great value in providing effective therapeutic intervention.

The dopamine transporter appears to be the site of action of cocaine, which binds the transporter with high affinity and specificity. The effect of the binding is to inhibit dopamine reuptake and therefore prolong the excitation of post-synaptic dopaminergic neurons. The sensations of euphoria and addiction to cocaine are believed to result from its dopamine transporter binding property. Research to improve understanding of the short and long-term effects on brain biochemistry, physiology and possibly anatomy depends on having suitable tracer compounds for quantitative and qualitative determination of dopamine transporter and for imaging under conditions of acute dosage, withdrawal and therapy.

SUMMARY OF THE INVENTION

Novel compounds are provided having the general structure:

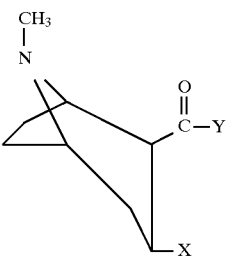

where

X in β configuration is phenyl, naphthyl; 2,3 or 4-iodophenyl; 2,3 or 4-(trimethylsilyl)phenyl; 3,4,5 or 6-iodonaphthyl; 3,4,5 or 6-(trimethylsilyl)naphthyl; 2, 3 or 4-(trialkyl-stannyl)phenyl; or 3,4,5 or 6-(trialkylstannyl)napthyl Y in β configuration is $Y_1$ or $Y_2$ where $Y_1$ is 2-fluoroethoxy, 3-fluoropropoxy, 4-fluorobutoxy,
2-fluorocyclopropoxy, 2 or 3-fluorocyclobutoxy,
R, S 1'-fluoroisopropoxy, R 1'-fluoroisopropoxy,
S 1'-fluoroisopropoxy, 1', 3'-difluoroisopropoxy,
R, S 1'-fluoroisobutoxy, R 1'-fluoroisobutoxy,
S 1'-fluoroisobutoxy, R, S, 4'-fluoroisobutoxy,
R 4'-fluoroisobutoxy, S 4'-fluoroisobutoxy, or
1', 1'-di(fluoromethyl)isobutoxy, and $Y_2$ is 2-methanesulfonyloxy ethoxy, 3-methanesulfonyloxy
propoxy, 4-methanesulfonyloxy butoxy,
2-methanesulfonyloxy cyclopropoxy,
2 or 3-methanesolfonyloxy cyclobutoxy,
1'methanesulfonyloxy isopropoxy, 1'-fluoro,
3'-methanesulfonyloxy isopropoxy,
1'-methanesulfonyloxy, 3'-fluoro isopropoxy,
1'-methanesulfonyloxy isobutoxy, or
4'-methanesulfonyloxy isobutoxy.

The compounds are able to bind strongly and with high specificity to dopamine transporter protein. Either of the halogen substituents can be radiolabeled by means of a rapid and specific labeling reaction suitable for labeling with short-lived isotopes such as [$^{18}$F], useful for PET imaging, or [$^{123}$I ], useful for SPECT imaging. The same compound is therefore useful for studies using several different analytical methods. Rapid synthetic reactions have been devised to prepare the above compounds in high yield and with high specific activity. In order to provide kits to prepare the compounds in situ, i.e., near a local source of the desired isotope, novel precursors are also provided, suitable for rapid fluorination by nucleophilic substitution, or for rapid iodination.

Compounds of the invention are useful for diagnostic imaging of the brain, in particular those regions having dopaminergic neurons. Such imaging is useful for differential diagnosis of Parkinson's disease and for the monitoring of addictive disorders related to abuse of cocaine and treatment thereof.

DETAILED DESCRIPTION OF THE INVENTION

Compounds of the invention provide substantially improved PET imaging for areas of the brain having dopaminergic neurons. All the available positron-emitting isotopes which could be incorporated into a biologically-active compound have short half-lives. The practical utility of such labeled compounds is therefore dependent on how rapidly the labeled compound can be synthesized, the synthetic yield and the radiochemical purity of the final product. Even the shipping time from the isotope source, a cyclotron facility, to the hospital or laboratory where PET imaging is to take place, is limited. A rough calculation of the useful distance is about two miles per minute of half-life. Thus [$^{11}$C], with a half-life of 20.5 m is restricted to about a 40 mile radius from a source whereas compounds labeled with [$^{18}$F] can be used within about a 200 mile radius. Further requirements of an [$^{18}$F]-labeled compound are that it have the binding specificity for the receptor or target molecule it is intended to bind, that non-specific binding to other targets be sufficiently low to permit distinguishing between target and non-target binding, and that the label be stable under conditions of the test to avoid exchange with other substances in the test environment. More particularly, compounds of the invention must display adequate binding to dopamine transporter while failing to bind to any comparable degree with other tissues or cells. Furthermore, the fluorine or iodine label must not be labile or unstable such that significant amounts appear in, e.g. bone or thyroid, respectively.

A partial solution to the stringent requirements for PET imaging is to employ γ-emitting isotopes in SPECT imaging. [$^{123}$I ] is a commonly used isotopic marker for SPECT, having a half-life of 13 hours for a useful range of over 1000 miles from the site of synthesis. Compounds of the invention can be rapidly and efficiently labeled with [$^{123}$I] for use in SPECT analysis as an alternative to PET imaging. Furthermore, because of the fact that the same compound can be labeled with either isotope, it is possible for the first time to compare the results obtained by PET and SPECT using the same tracer.

In vivo distribution of a compound of the invention, [$^{18}$F]-2β-carbo-2'-fluoroisopropoxy-3β-(4-iodophenyl) tropane (FIPIT) 8 (X=4-iodophenyl; Y=1'fluoroisopropoxy) was measured, as well as brain PET imaging to determine suitability of the compound as a label. Also, in vitro binding studies were conducted, measuring the ability of FIPIT to displace [$^3$H]WIN 35,428 (III) in a rat striatal homogenate preparation. These studies provided a calculated binding constant for FIPIT 8 with dopamine transporter of 1.13 nM. PET imaging using [$^{18}$F]-FIPIT administered to a rhesus monkey showed that the basal ganglia (striatum) was the region of highest uptake in the brain and also showed prolonged retention with clear visualization at 190 min following injection. Region of interest measurements determined striatal to cerebellum ratios to be 3.0 at 190 min post administration. In the in vivo distribution studies, the distribution of radioactivity was expressed as percent dose per gram in tissues of unfasted male Sprague Dawley rats at 2 min, 30 min, 60 min and 120 min after intravenous administration of [$^{18}$F] FIPIT 8. The results are shown in Table I. The initial level of accumulation of radioactivity in the striatum, a region rich in dopamine transporters, after injection of [$^{18}$F] FIPIT 8 was high, 0.84% of injected dose/gram at 2 min, and decreased slowly to 0.50% of injected dose/gram at 120 min. The agent, however, exhibited a rapid washout in all other brain regions. The cerebellum and cortex exhibited a maximum at 2 min 0.76% dose/gram and 0.98% dose/gram respectively. However, the amount of radioactivity in the cerebellum and cortex at 120 min decreased to only 0.14% dose/gram and 0.26% dose/gram respectively resulting in a striatum to cerebellum ratio of 3.71 and a striatum to cortex ratio of 2.0. The bone radioactivity showed no increase from 0.28% dose/gram at 2 min, to 0.25% dose/gram at 120 min, which demonstrated the stability of the 2β-fluoroisopropyl group to significant in vivo defluorination.

TABLE I

Distribution of Radioactivity in Tissues of Unfasted Male Sprague Dawley Rats following Intravenous Administration of [$^{18}$F] FIPIT (8)

Mean % Injected Dose/Gram (Average of 4 Rats)

| Organ | 2 min | 30 min | 60 min | 120 min |
|---|---|---|---|---|
| Blood | 0.14 | 0.03 | 0.03 | 0.04 |
| Heart | 1.70 | 0.14 | 0.10 | 0.12 |
| Muscle | 0.12 | 0.13 | 0.04 | 0.08 |
| Lung | 6.21 | 0.61 | 0.40 | 0.46 |
| Kidney | 2.61 | 0.85 | 0.44 | 0.3 |
| Spleen | 1.58 | 0.64 | 0.40 | 0.38 |
| Liver | 1.5 | 3.89 | 5.20 | 4.46 |
| Testis | 0.14 | 0.68 | 0.17 | 0.19 |
| Bone | 0.28 | 0.21 | 0.17 | 0.25 |
| Brain (B) | 0.83 | 0.53 | 0.31 | 0.28 |
| Striatum (St) | 0.84 | 0.73 | 0.58 | 0.50 |
| Cerebell (C) | 0.76 | 0.3 | 0.16 | 0.14 |
| Cortex (Cx) | 0.98 | 0.53 | 0.28 | 0.26 |
| St/C | 1.12 | 2.42 | 3.63 | 3.71 |
| St/Cx | 0.86 | 1.38 | 2.13 | 2.00 |

Synthesis of FIPIT 8 was accomplished in a series of steps beginning with cocaine (I) as starting material and hydrolysis to yield ecgonine (Reactions 1–8). The entire synthesis is described in detail in Examples 1–9. Synthesis of [$^{18}$F]-FIPIT 8 is also described (Reactions 10 and 11) as is synthesis of [$^{123}$I ]-FIPIT 8 (Reactions 9, 14 and 15). The final reaction step for synthesis of [$^{18}$F] FIPIT 8 from the 1-methanesulfonyloxy isopropyl precursor 10 (Reaction 11) and purification by HPLC can be accomplished in 2 hours. In general, [$^{18}$F] labelling can be

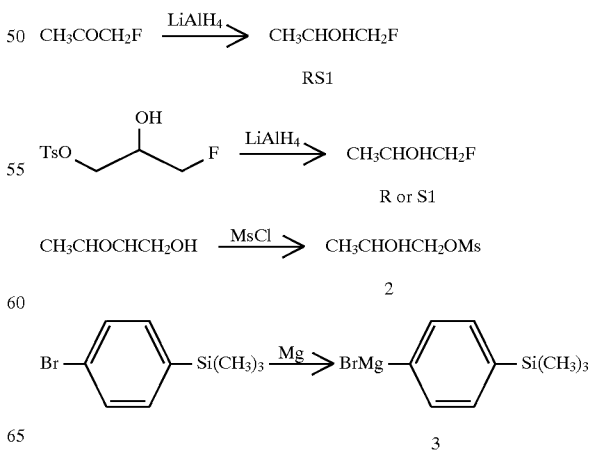

-continued
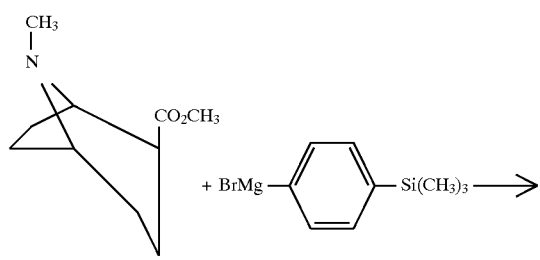
4
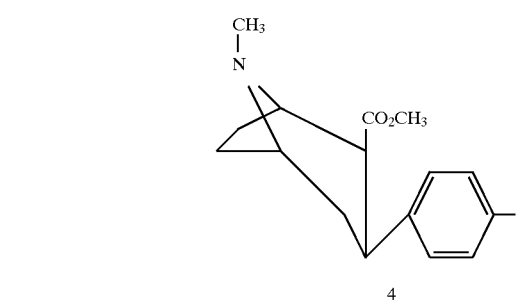
4
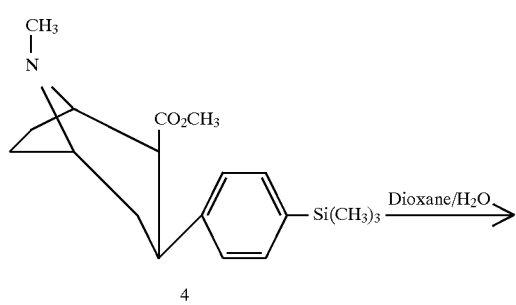
5
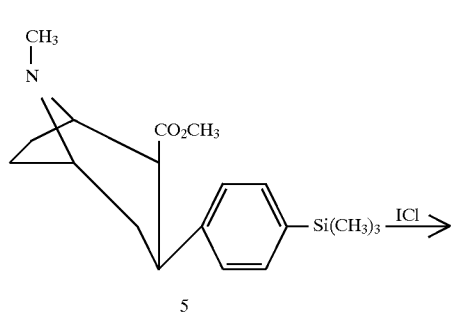
5
-continued
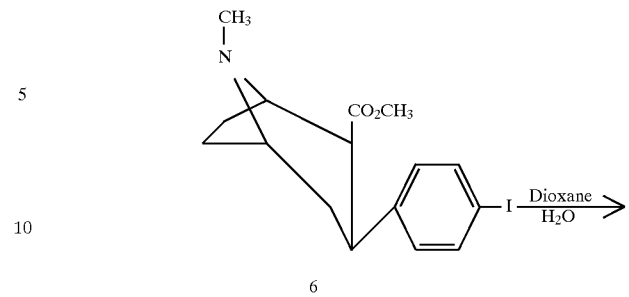
6
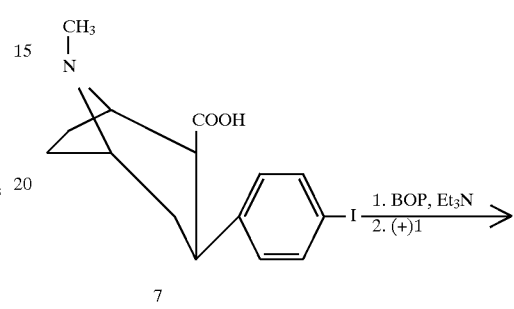
7
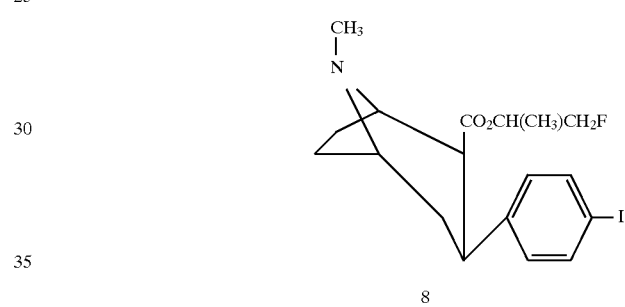
8
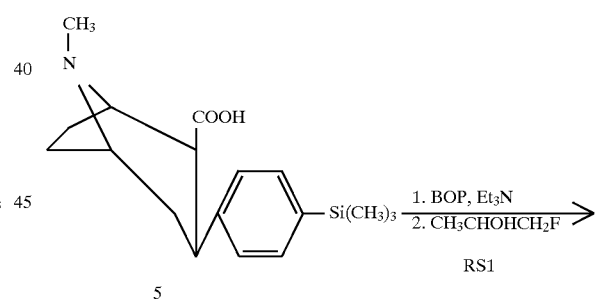
5
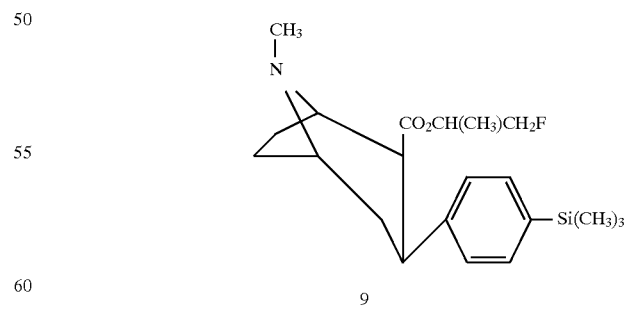
9

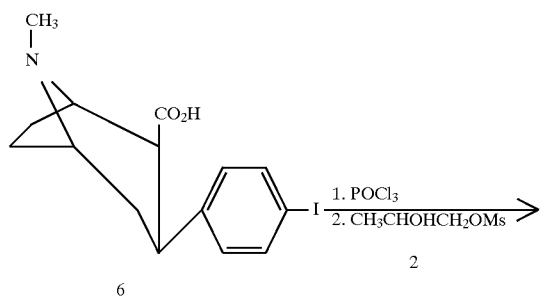
6
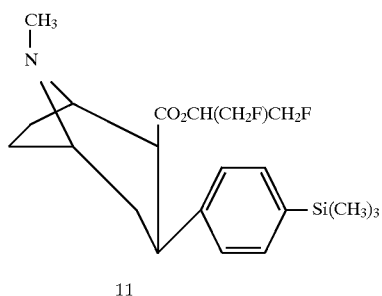
11
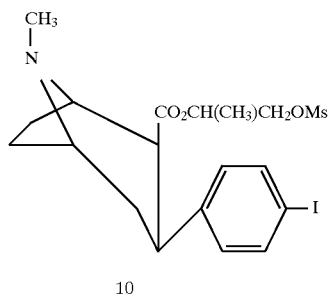
10
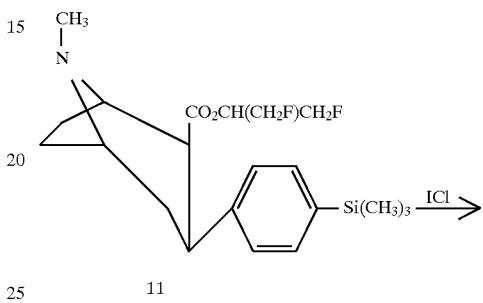
11
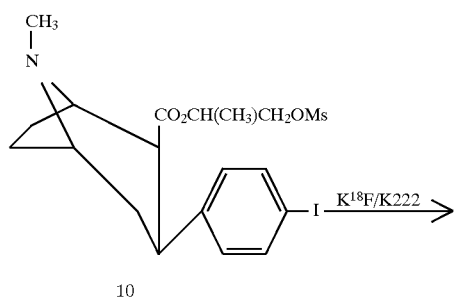
10
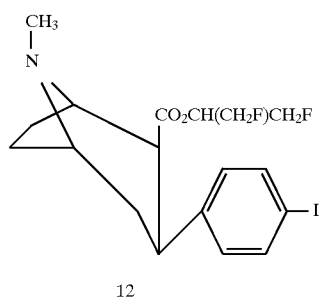
12
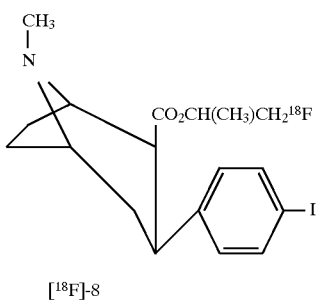
[18F]-8
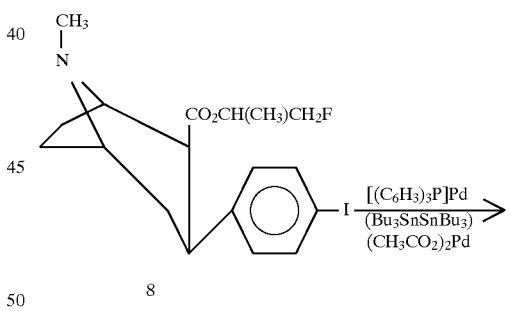
8
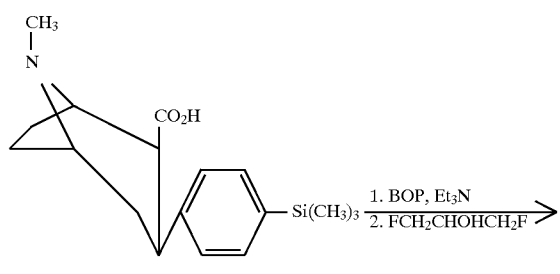
5
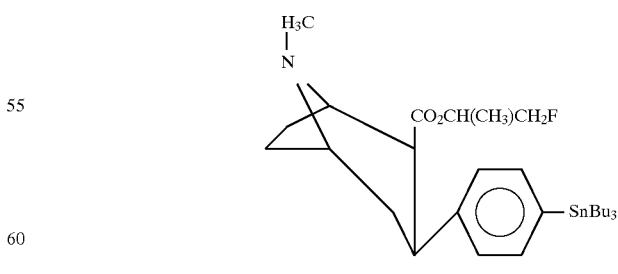
13

-continued

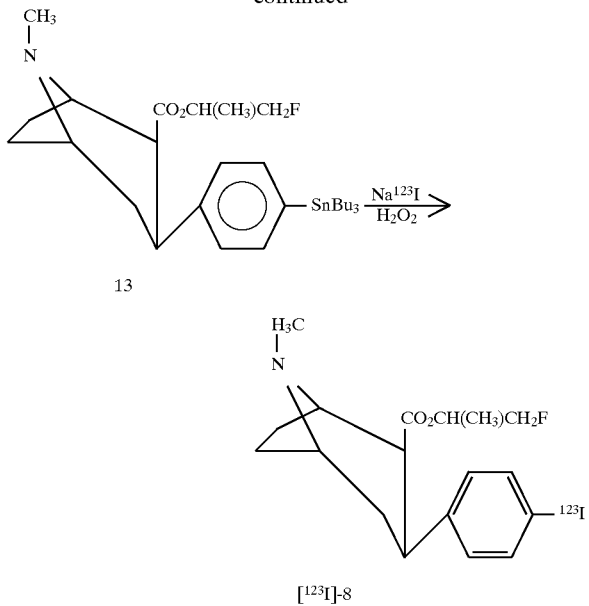

rapidly achieved by a nucleophilic substitution reaction starting with an appropriate methanesulfonyloxy alkyl precursor, [$^{18}$F] KF and a phase transfer catalyst, see example 12. The synthesis of additional compounds of the invention can be accomplished by variations of the synthesis of FIPIT 8, with substitution of the appropriate precursors, as is well known in the art and described in the examples. (See also, e.g., Reactions 12 and 13.) A labeling kit can be provided to facilitate on-site radiolabeling, especially where the label is [$^{18}$F]. Such a kit can include a precursor compound of the invention (where Y=Y$_2$) and a phase transfer catalyst. Optionally, such a kit can also contain prepacked columns for use in purifying the reaction products. The end user would then obtain K$^{18}$F from the closest local source for use in the labeling reaction. A kit for [$^{123}$I] labeling can be provided for rapid onsite labeling. Such a kit contains a precursor such as a trimethylsilylphenyl (e.g., Compound 11), trimethylsilylnaphthyl, trialkylstannylphenyl (e.g. Compound 13), or trialkylstannylnaphthyl precursor. Rapid labeling can be accomplished as described in the Examples or by reactions known in the art.

Compounds of the invention, labeled with [$^{18}$F] make it possible to carry out positron emission tomography (PET) with a novel [$^{18}$F] tracer available in higher specific activity and higher signal strength than previously available. These advantages are in part due to the rapid synthesis which consumes a smaller portion of the isotope's useful decay life. At the same time, the lower energy of [$^{18}$F] emissions compared to other available PET tracers permits higher resolution imaging. Furthermore, PET imaging carried out with compounds of the invention can be directly compared with single photon emission (SPECT) imaging using what is chemically the same compound as tracer. Therefore, improved methods for PET and SPECT are now available, by administering to a subject (which can be a human or animal, for experimental and/or diagnostic purposes) an image-generating amount of a compound of the invention, where X is 2, 3 or 4-iodophenyl or 3, 4, 5 or 6 iodonaphthyl, Y is Y$_1$ labeled with [$^{18}$F] and then measuring the distribution of the compound by PET. An image-generating amount is that amount which is at least able to provide an image in a PET scanner, taking into account the scanner's detection sensitivity and noise level, the age of the isotope, the body size of the subject and route of administration, all such variables being known and accounted for by calculations known to those skilled in the art without resort to undue experimentation.

Similarly, an improved SPECT imaging method is carried out by administering to a subject an image-generating amount of a compound of the invention where X is 2, 3 or 4 iodophenyl or 3, 4, 5 or 6 iodonaphthyl labeled with [$^{123}$I] and Y is Y$_1$, then measuring the distribution of the compound by SPECT imaging. An advantage of the improved method is that image data obtained by the method can be directly compared and correlated with PET data obtained using a chemically identical (except for isotopic label) tracer.

It will be understood that compounds of the invention can be labeled with an isotope of any atom or combination of atoms in the structure. While [$^{18}$F] and [$^{123}$I] have been emphasized herein as being particularly useful for PET and SPECT imaging, other uses are contemplated and will be apparent to those skilled in the art. For example, without limitation, compounds of the invention can be labeled with [$^{14}$C] to provide a tracer useful for biochemical studies of dopamine transporter. In addition, the binding studies reported herein demonstrate a pharmacological effect of compounds of the invention which can be utilized for physiological and behavioral studies and therapies, as will be apparent to those skilled in the art.

EXAMPLE 1

RS 1-Fluoro-2-propanol 1

A solution of fluoroacetone (1.0 g, 13 mmol) in 5 mL of anhydrous ether was added dropwise to a stirred suspension of LiAlH$_4$ (131 mg, 3.25 mmol) in 15 mL of anhydrous ether at −70° C. over a period of 1 min (Reaction 1). The reaction mixture was allowed to warm to room temperature. The mixture was stirred at 40° C. for 10 min, then cooled to room temperature and acidified to pH 3 with 10% H$_2$SO$_4$ solution. The aqueous phase was separated and extracted with ether (4×15 mL). The combined organic phase was washed with saturated NaHCO$_3$, brine, dried over anhydrous MgSO$_4$ and concentrated in vacuo to give crude product, 460 mg.

The product was used without further purification.

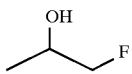

1-Fluoro-2-propanol 1

This compound was isolated as a colorless liquid, bp 105° C., $^{13}$C NMR (CDCl$_3$) δ 17.45 (d,J=7.55 Hz, CH$_3$) 66.28 (d, J=19.6 Hz, CHOH), 87.70 (d,J=170 Hz, C23); $^1$H NMR (CDCl$_3$) δ 1.18 (dd,J=1.5, 3.6 Hz, 3H), 3.447 (s,1H), 3.98–4.12 (m,1H), 4.236 (ddd,J=6.9, 9.3, 48 Hz, 1H), 4.353 (ddd,J=3.0, 9.3, 47 Hz, 1HO.

EXAMPLE 2

(R or S)-1-Fluoro-2-propanol 1

To a well stirred solution of either (S) 1-fluoro-3-tosyloxy-2-propanol or (R) 1-fluoro-3-tosyloxy-2-propanol (prepared from the commercially available, chirally pure 1,1-dimethyl-3-hydroxymethyl-dioxolane precursor via the route of Kawakami et al, J. Org. Chem. 47:3581–3585; 1982) in 10 mL ether at −78° C. was added 1.72 mL (1.05 H$^-$ equiv) of a 1M LiAlH$_4$ solution (in THF) (Reaction 2).

The solution was allowed to slowly warm to room temperature stirred for 1 h, and quenched with 2 mL water and 6 mL 1 N NaOH. The solution was filtered through a bed of celite and the aqueous phase removed. The celite bed was washed with a few mLs of ether and the aqueous layer was extracted with this wash. The combined organic layers were dried with sodium sulfate and the solvent removed with the use of a short path distillation head. The last fraction distilled remaining in the pot contained the fluoropropanol as well as THF and some residual ether, the amount of which was determined by NMR to estimate the ratios of the compounds present.

EXAMPLE 3

1-Methanesulfonoxy-2-propanol 2

Methanesulfonyl chloride (7.74 mL, 0.1 mL) was added dropwise to a solution of 1,2-propanediol (9.13 g, 0.12 mol) and $Et_3N$ (14 mL, 0.1 mol) in 65 mL of $CH_2Cl_2$ at $-10°$ C. (Reaction 3). After 1.5 h at $0°$ C. the resulting reaction mixture was quenched with ice-$H_2O$. The aqueous phase was extracted with $CH_2Cl_2$ (3×25 mL). The combined $CH_2Cl_2$ extracts were washed with 1 N HCl, 50% $NaHCO_3$, brine, dried over anhydrous $MgSO_4$ and concentrated in vacuo to give 12 g of crude product. The aqueous phase was reextracted with $CH_2Cl_2$ (4×20 mL) and worked up as above to give an additional 2 g of product. Total crude product 14 g, 90% yield. 2 g of crude product was purified by flash chromatography on silica with 20% ether in $CH_2Cl_2$ to give 1.67 g of pure product. TLC with 20% ether in $CH_2Cl_2$ Rf=0.34.

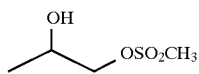

1-Methanesulfonoxy-2-propanol 2

This compound was isolated as a colorless liquid, $^{13}C$ NMR ($CDCl_3$) δ 18.46 ($CH_3$), 37.20 ($SO_2CH_3$) 65.36 (CHOH), 74.45 ($CH_2$); $^1H$ NMR ($CDCl_3$) δ 1.235 (d,J=6.0 Hz, 3H), 3.091 (s, 3H), 3.273 (broad, 1H), 4.03–4.22 (m, 3H).

EXAMPLE 4

4-Trimethylsilylphenyl magnesium bromide 3

A 100 mL round bottom. flask equipped with a reflux condenser was flame dried and cooled under Argon. To this was added 6 g of magnesium turnings and 40 mL of anhydrous ethyl ether. 6 g (26.2 mmol) of 4-(trimethylsilyl) bromobenzene was added and the reaction stirred until it spontaneously warmed and became cloudy (Reaction 4). Additional ether was added to moderate the reaction, which was allowed to proceed overnight. The reaction mixture salts were allowed to settle and the ether layer removed by syringe and used immediately.

EXAMPLE 5

2β-Carbomethoxy-3β-(4-Trimethylsilylphenyl) tropane CSiT 4

(−)-Anhydroecognine methyl ester (1.09 g, 6.02 mmol) was dissolved in 20 mL of anhydrous ether and added to 4-trimethylsilylphenyl magnesium bromide (26 mmol in 50 mL ether) at $-40°$ C. as described earlier (Clark et al (1973) supra) (Reaction 5). The solution was stirred at this temperature for 3 h, then cooled to $-78°$ C. and treated with 5 mL of trifluoroacetic acid in 20 mL ether. The reaction mixture was worked up as previously reported (Carrol et al. (1990) *J. Med. Chem.* 34:2719–2725). The crude product was purified by flash chromatography (1% triethylamine in ether) to give 518 mg (32%) as a white solid. A single component was detected by TLC (EtOAc/MeOH/$NH_4OH$ 3/1/0.04):

$^1H$ NMR (300 MHz, $CDCl_3$: d 7.43 (d, J=7.8 Hz, 2H, Ar), d 7.25 (d,J=7.8 Hz, Ar), d 3.55 (1H, H-1), d 3.48 (s, $OCH_3$), d 3.34 (1H, H-5), d 2.95 (m, 1H, H-3), d 2.90 (m, 1H, H-2), d 2.58 (t, 1H, H-4$_{eq}$), d 2.21 (s, 3H, N-$CH_3$), d 2.05 (m, 1H), d 1.54–1.71 (m, 4H), d 0.202 (s,9H); $^{13}C$ NMR (75 MHz, APT exp., $CDCl_3$): d 171.989 (u), d 143.524 (u), d 137.133 (u), d 132.941 (d), d 126.686 (d), d 65.269 (d), d 62.193 (d), d 52.543 (d), d 50.993 (d), d, d 41.892 (d), d 33.793 (u), d 33.706 (d), d 25.806 (u), d 25.096 (u), d −1.161 (d); MS: (m/z 331($M^+$, 20%)). Anal. C, H, N.

EXAMPLE 6

2β-Carboxy-3β-(4-Trimethylsilylphenyl)tropane CSiT-acid 5

A round bottom flask filled with a solution of 254 mg of 2-βcarbomethoxy-3β-(4-trimethylsilylphenyl)tropane in 10 mL of 1:1 water/dioxane was heated to a gentle reflux for two days (Reaction 6). The solvent was then removed and the white residue was triturated with hot ethyl acetate twice. The remaining solid was dried under in vacuo to yield 230 mg of CSiT-acid 5 (94%) as a white solid.

EXAMPLE 7

2β-Carbomethoxy-3β-(4-Iodophenyl)tropane 6

50 mg of 2β-carbomethoxy-3β-(4-trimethylsilylphenyl) tropane was dissolved in 5 ml of $CCl_4$ at ambient temperature. To this was added 40 mg of iodine monochloride after which the solution was stirred for 2 h, then poured into 20 mL of 10% sodium thiosulfate (Reaction 7). The two phase solution was shaken until the dark color disappeared, made basic with saturated sodium bicarbonate, and the organic layer separated. The aqueous layer was extracted three times with 10 mL portions of $CHCl_3$ and the combined organic layers were then washed with brine, dried over sodium sulfate, and concentrated in vacuo. The residue was dissolved in a small portion of ether and chromatographed using a flash $SiO_2$ column (10"×½", ether/hexane ½) and the eluents concentrated to yield 53 mg of (91%) CIT. No isomerization of the ester moiety was detected by TLC or NMR.

EXAMPLE 8

2β-Carboxy-3β-(4-Iodophenyl)tropane, CIT-acid 7

A round bottom flask filled with a solution of 100 mg of 2β-Carbomethoxy-3β-(4-Iodophenyl)tropane in 10 mL of 1:1 water/dioxane was heated to a gentle reflux for two days. The solvent was then removed and the white residue was triturated with hot ethyl acetate twice. The remaining solid was dried under in vacuo to yield 90 mg of CIT-acid 7, (93%) as a white solid.

EXAMPLE 9

2β-(1'-Fluoroisopropoxy))3β-(4-Iodophenyl)tropane FIPIT 8

110 mg of 2β-(2-fluoroisopropoxy)-3β-(4-trimethylsilyl-phenyl)tropane 9 was dissolved in 10 mL of $CCl_4$. To this was added 60 mg iodine monochloride and the reaction stirred for 2 h. The solution was poured into 10% sodium thiosulfate and shaken until the dark color disappeared, made basic with saturated sodium bicarbonate, the organic layer separated, and the aqueous layer extracted several times with 20 mL portions of methylene chloride. The combined organic layers were dried with sodium sulfate and concentrated in vacuo. The resulting oil was purified using flash $SiO_2$ column (6"×½", ether) to yield 68 mg (54%) of FIPIT 8 as a white solid.

$^1$H NMR (300 MHz, $CDCl_3$: d7.56 (d, J=8.4 Hz, 2H, Ar), d 7.00 (d, J=8.4 Hz, 2H, Ar), d 5.0 (m, 1H, 2'), d 3.95 (dm, 2H, a-F), d 3.58 (1H, H-1), d 3.34 (1H, H-5), d 2.95 (m, 1H, H-3), d 2.90 (m, 1H, H-2), d 2.53 (dt, 1H, H-4$_{eq}$), d 2.22 (s, 3H, N—$CH_3$), d 2.05 (m, 1H, 4$_{eq}$), 1.54–1.71 (m, 4H); d 1.08 (dd, J=7 Hz, 3H,3'), d 1.14 (dd, J=7 Hz, 3' mnr isomer);

EXAMPLE 10

2β-(1' Fluoroisopropoxy)-3β-(4-Trimethylsilyl-phenyl)tropane FIPSiT 9

A solution of 88 mg of CSiT-acid 5 was dissolved in 2 mL of acetonitrile. To this solution was added 123 BOP (benzotriazol-1-yloxy tris (dimethylamino) phosphonium hexafluorophosphate), 0.2 mL triethylamine, and 50 mg of 1-fluoro-2-propanol R, S or RS 1 (Reaction 9). The solution was stirred for 16 h and then diluted with 10 mL saturated sodium bicarbonate and extracted with 3 portions of ethyl ether (10 mL each). The combined organic layers were dried with sodium sulfate and concentrated in vacuo. The resulting oil was purified using flash $SiO_2$ column (6"×½", ether) to yield 80 mg (76%) of a single diastereomer of FIPSiT as a white solid.

$^1$H NMR (300 MHz, $CDCl_3$: d 7.56 (d, J=8.4 Hz, 2H, Ar), d 7.00 (d, J=8.4 Hz, 2H, Ar), d 5.0 (m, 1H, 2'), d 3.95 (dm, 2H, a-F), d 3.58 (1H, H-1), d 3.34 (1H, H-5), d 2.95 (m, 1H, H-3), d 2.90 (m, 1H, H-2), d 2.53 (dt, 1H, H-4$_{eq}$), d 2.22 (s, 3H, N—$CH_3$), d 2.05 (m, 1H, 4$_{eq}$), d 1.54–1.71 (m, 4H); d 1.02 (dd, J=7 Hz, 17 Hz, 3H, 3'), d 1.06 (dd, 3' mnr isomer);

EXAMPLE 11

R,S 3β-(4'-Iodophenyl)tropan-2β-carboxylic acid 1-methanesulfonoxy isoDropyl ester 10

To 3β-(4'-Iodophenyl)tropan-2β-carboxylic acid 6 (74 mg, 0.20 mmol) was added $POCl_3$ (1.0 mL, 10 mmol) at 0° C. The resulting mixture was stirred at ambient temperature for 4 h and then evaporated. Toluene, 3 mL, was added and the reaction mixture was evaporated to dryness. The residue was flushed with argon. To the residue was added sequentially $CHCl_3$, 5 mL, Pyridine, 0.2 mL and 1-methanesulfonoxy-2-propanol 2 (310 mg, 2.0 mmol) (Reaction 10). The reaction mixture was stirred at 0°–25° C. for 2.5 h. The resulting reaction mixture was quenched with 15 mL of $H_2O$. The aqueous phase was extracted with $CHCl_3$ (10 mL) and $CH_2Cl_2$ (3×15 mL). The combined extracts were washed with brine and dried over anhydrous $MgSO_4$ and concentrated in vacuo to give crude product. The crude product was purified by flash chromatography on silica with 6% MeOH in $CH_2Cl_2$ to give 57 mg (40%) of pure product. TLC with 6% MeOH in $CH_2Cl_2$ Rf=0.12.

This compound was isolated as a thick sticky oil.

$^1$H NMR ($CDCl_3$) δ 1.090 (d,J=6.6 Hz, 3H), 1.57–1.85 (m,4H), 2.10–2.36 (m,1H), 2.85–3.16 (m,2H), 3.023 (s, 3H), 3.38–3.68 (m,2H), 4.077 (dd,J=5.4, 10.5 Hz, 1H), 4.205 (dd,J=3.0, 11.1Hz, 1H), 4.97–5.09 (m, 1H), 7.004 (d,J=8.1 Hz, 2H), 7.589 (d,J=8.4 Hz, 2H).

EXAMPLE 12

Fluorine-18 labeled2β-carbo-1'-fluoroisopropoxy-3β-(4-iodophenyl)tropane (FIPIT) 8

Approximately 350 mg of $^{18}O$ water containing 840 mCi of no carrier added $^{18}F$ was delivered to a vial inside a remotely controlled robotic chemistry unit. To this vial was added 1 mL of a solution containing 10 mg K-222 4, 7, 13, 16, 21, 24-Hexaoxa-1, 10-diazabicyclo [8,8,8] hexacosane ("Kryptofix", Trademark, Aldrich Chemical Co., Milwaukee, Wis.) as a phase transfer catalyst, 1 mg potassium carbonate, 0.05 mL water and 0.95 mL MeCN. The solution was heated at 118° C. for 3.5 minutes after which an additional portion of 3 mL MeCN was added and evaporated 7 minutes to dry the fluoride. The vial was cooled to room temperature and 3.0 mg of R,S 3β-(4'-Iodophenyl)-tropan-2β-carboxylic acid 1-methanesulfonoxy isopropyl ester 10 in 1.0 mL MeCN (Reaction 11). The solution was heated to 100° C. for 6 minutes, cooled to room temperature, and passed through a Waters classic $SiO_2$ sep-pak into a 12 mL conical glass vessel. The sep-pak was rinsed with 8 mL 10% MeOH in $CH_2Cl_2$ and the resulting solution was concentrated by heating at 118° C. The residue was dissolved in 1.5 mL of 85/15/0.1% MeOH/water/triethylamine and loaded onto a reverse phase prep column. (Nova Pak, Trademark, Waters Associates, Milford, Mass., 25 mm×100 mm, flow rate 6 mL/min). The fraction of FIPIT 8 contained 30.5 mCi (4.9%, based on E.O.B.) of the desired product. Radio-TLC and radio-HPLC analysis showed these fractions to have a radiochemical purity of greater than 99% and to have a specific activity of at least $2\times10^3$ Ci/mmol. The fractions containing the greatest radioactivity were concentrated in vacuo, dissolved in sterile saline with 10% EtOH, and filtered through a Millipore 0.2 micron filter for in vivo studies. The entire reaction and purification required only 2 hours.

EXAMPLE 13

2β-(1',3'-Difluoroisopropoxy)-3β-(4-Trimethylsilyl-phenyl)tropane DFIPSiT 11

A solution of 20 mg of CSiT-acid 5 in 2 mL acetonitrile was treated sequentially with 30 mg BOP reagent, 20 mL triethylamine, and 10 mL of 1,3-difluoro-2-propanol and then stirred at room temperature for 16 h (Reaction 12). The solution was then diluted with 10 mL saturated sodium bicarbonate and extracted with 4 portions of $CH_2Cl_2$ (5 mL each). Then combined organic extracts were combined, dried over sodium sulfate, and concentrated in vacuo. The resulting oil was chromatographed using a 6"×½" silica flash column (ether/hexane ½ to ether) to yield 18 mg (72%) of DFIPSiT 11 as a clear oil.

$^1$H NMR (300 MHz, $CDCl_3$: d 7.43 (d, J=7.8 Hz, 2H, Ar), d 7.24 (d, J=7.8 Hz, 2H, Ar), d 5.03 (ddt, 1H, 2'), d 4.5 (dd, 4H, a-F), d 3.61 (1H, H-1), d 3.37 (1H, H-5), d 3.02 (m, 1H, H-3), d 3.0 (m, 1H, H-2), d 2.58 (t, 1H, H-4$_{eq}$), d 2.22 (s, 3H, N—$CH_3$), d 2.05 (m, 1H), d 1.54–1.71 (m, 4H), d 0.23 (s, 9H); $^{13}$C NMR (75 MHz, $CDCl_3$): d 170.543, d 143.379, d 137.557, d 133.081, d 126.668, d 65.322, d 62.263, d 52.485, d 41.846, d 33.752, d 33.584, d 25.309, d 25.777, d-1.102; MS: (m/z 395 ($M^+$, 15.5%)). HRMS calc. for $C_{21}H_{31}F_2SiO_2N$: 395.2092, found 395.2104.

EXAMPLE 14

2β-(1',3'-Difluoroisopropoxy)-3β-(4-Iodophenyl)-tropane DFIPIT 12

10 mg of 2β-(1',3'-difluoroisopropoxy)-3β-(4-trimethylsilyl-phenyl)tropane 11 was dissolved in 5 ml of CCl$_4$ at ambient temperature. To this was added 5 mg of iodine monochloride after which the solution was stirred for 2 h, then poured into 20 mL of 10% sodium thiosulfate (Reaction 13). The two phase solution was shaken until the dark color disappeared, made basic with saturated sodium bicarbonate, and the organic layer separated. The aqueous layer was extracted three times with 10 mL portions of CHCl$_3$ and the combined organic layers were then washed with brine, dried over sodium sulfate, and concentrated in vacuo. The residue was dissolved in a small portion of ether and chromatographed using a flash SiO$_2$ column (10×½", ether/hexane ½) and the eluents concentrated to yield 7 mg of (60%) DFIPIT 12. No isomerization of the ester moiety was detected by TLC or NMR.

$^1$H NMR (300 MHz, CDCl$_3$: d 7.57 (d, J=8.4 Hz, 2H, Ar), d 6.98 (d, J=8.4 Hz, 2H, Ar), d 5.03 (ddt, 1H, 2'), d 4.4 (dd, 4H, a-F), d 3.64 (1H, H-1), d 3.41 (1H, H-5), d 2.95 (m, 1H, H-3), d 3.0 (m, 1H, H-2), d 2.58 (l,1H, H-4$_{eq}$), d 2.26 (s, 3H, N—CH$_3$), d 2.05 (m, 1H), d 1.54–1.71 (m, 4H);

EXAMPLE 15

2β-carbo-1'-fluoroisopropoxy-3β-(4-tributylstannylphenyl)tropane 13

A solution of 2β-(1'-fluoroisopropoxy)-3β-(4-iodophenyl)tropane 8, 250 mg is dissolved in 10 mL of toluene under an Argon atmosphere. To the solution is added bis(tributyl)distannane (522 mg, 0.9 mmol), palladium (II) acetate (17 mg, 0.075 mmol), and tetrakis (triphenylphosphine) palladium (O) (3 mg, 0.003 mmol) (Reaction 14). The resulting reaction mixture is stirred and heated under reflux for 28 hr. The reaction mixture is cooled and applied to a 500 mL chromatography column containing silica gel slurried in diethyl ether. The product is purified by elution with 18:1 diethyl ether:triethylamine.

EXAMPLE 16

Iodine-123 labeled 2β-carbo-1'-fluoroisopropoxy-3β-(4-iodophenyl)troDane [$^{123}$I]8

Aqueous hydrogen peroxide (50 µL, 3% w/v) is added to a septum sealed vial containing 2β-carbo-1'-fluoroisopropoxy-3β-(4-tributylstannylphenyl)tropane 13 (50 µg) in 50 µL EtOH, 50 µL of 0.1N HCL, and 5 µL of [$^{123,125}$I] sodium iodide (no-carrier-added, sp. act. 200,000 Ci/mmol and 2,200 Ci/mmol respectively (Reaction 15). The reaction is allowed to proceed at ambient temperature for 30 min. The reaction is quenched with 0.1 mL of sodium bisulfite (300 mg/mL) basified pH=8.5 with saturated NaHCO$_3$ and is extracted with ethyl acetate (1×3 mL). The combined ethyl acetate extracts are dried by passage through an 0.2 cm×5 cm column of anhydrous sodium sulfate. The ethyl acetate is evaporated by a stream of nitrogen and the residue is dissolved in 50–100 µL of 100% EtOH. The radioiodinated solution is purified by HPLC using a reverse-phase column. The fractions containing the desired product are collected, condensed and extracted with ethyl aceate (3×1 mL). The combined ethyl acetate extracts containing the no-carrier-added product is evaporated by a stream of nitrogen and the residue is dissolved in 50–100 µL of 1000 EtOH.

We claim:

1. A kit for rapid synthesis of [$^{18}$F]-labeled compound for binding dopamine transporter, comprising (a) a compound having the structure

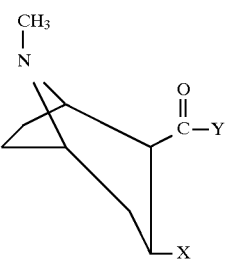

wherein

X in β configuration is 2,3 or 4-iodophenyl; or 3,4,5, or 6-iodophenyl

Y in β configuration is Y$_2$ wherein Y$_2$ is
2-methanesulfonyloxy ethoxy, 3 methanesulfonyloxy propoxy, 4-methanesulfonyloxy butoxy, 2-methanesulfonyloxy cyclopropoxy, 2 or 3-methanesolfonyloxy cyclobutoxy, 1'methanesulfonyloxy, 1'-fluoro, 3'-methanesulfonyloxy isopropoxy, 1'-methanesulfonyloxy, 3'-fluoro isopropoxy 1'-methanesulfonyloxy, or 4'-methanesulfonyloxy, isobutoxy, and (b) 4,7,13,16,21,24-Hexaoxa-1,10-diazabicyclo[8,8,8]hexacosane as a phase transfer catalyst whereby reaction of said compound with K[$^{18}$F] catalyzed by said catalyst yields an $^{18}$F-labeled compound for binding dopamine transporter.

2. A method for conducting positron emission tomography of a subject comprising administering to said subject an image-generating amount of a compound having the structure

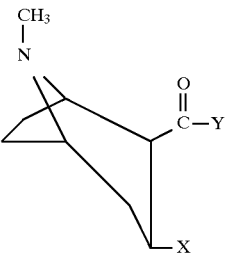

wherein

X is 2, 3 or 4-iodophenyl; or 3, 4, 5, or 6-iodophenyl, Y in β configuration is
2-fluoroethoxy, 3-fluoropropoxy, 4-fluorobutoxy, 2-fluorocyclopropoxy, 2 or 3-fluorocyclobutoxy, R,S 1'-fluoroisopropoxy, R 1'-fluoroisopropoxy, S 1'-fluoroisopropoxy, 1',3'-difluoroisopropoxy, R,S 1'-fluoroisobutoxy, R 1'-fluoroisobutoxy, S 1'-fluoroisobutoxy, R,S 4'-fluoroisobutoxy, R 4'-fluoroisobutoxy, S 4'-fluoroisobutoxy, or 1',1'-di (fluoromethyl)isobutoxy, comprising [$^{18}$F], and measuring the distribution within the subject of said compound by positron emission tomography.

3. A method for conducting single photon emission imaging of a subject comprising administering to said subject an image-generating amount of a compound having the structure

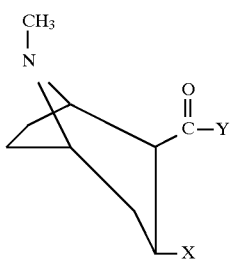

wherein

X is 2, 3 or 4-iodophenyl; or 3, 4, 5 or 6-iodonaphthyl comprising [$^{123}$I], Y in β configuration is 2-fluoroethoxy, 3-fluoropropoxy, 4-fluorobutoxy, 2-fluorocyclopropoxy, 2 or 3-fluorocyclobutoxy, R,S 1'-fluoroisopropoxy, R 1'-fluoroisopropoxy, S 1'-fluoroisopropoxy, 1',3'-difluoroisopropoxy, R,S 1'-fluoroisobutoxy, R 1'-fluoroisobutoxy, S 1'-fluoroisobutoxy, R,S 4'-fluoroisobutoxy, R 4'-fluoroisobutoxy, S 4'-fluoroisobutoxy, or 1',1'-di(fluoromethyl)isobutoxy, and measuring the distribution within the subject of said compound by single photon emission imaging.

* * * * *

UNITED STATES PATENT AND TRADEMARK OFFICE
CERTIFICATE OF CORRECTION

PATENT NO. : 5,888,475

DATED : March 30, 1999

INVENTOR(S) : Goodman et al.

It is certified that error appears in the above-identified patent and that said Letters Patent is hereby corrected as shown below:

At column 1, line 52, delete "[·O]" and replace with --[$^{15}$O]--.
At column 2, line 19, delete "[$^{123}$]" and replace with --[$^{123}$I]--.
At column 8, line 57, delete "CH$_3$CHOCHCH$_2$OH" and replace with --CH$_3$CHOHCH$_2$OH--
At column 10, line 22, reaction 7, delete "2.(+)1" and replace with --2.($\pm$)1--.
At column 17, line 43, delete "isoDropyl" and replace with --isopropyl--.
At column 19, line 41, delete "troDane" and replace with --tropane--.

In the claims:

At column 20, claim 1, line 26, insert "," at the end of the line.
At column 20, claim 1, line 27, delete "," at the end of the line.

Signed and Sealed this

Fifteenth Day of February, 2000

Q. TODD DICKINSON

*Attest:*

*Attesting Officer*  *Commissioner of Patents and Trademarks*

UNITED STATES PATENT AND TRADEMARK OFFICE
CERTIFICATE OF CORRECTION

PATENT NO.      : 5,888,475                                                         Page 1 of 1
DATED           : March 30, 1999
INVENTOR(S)     : Goodman et al.

It is certified that error appears in the above-identified patent and that said Letters Patent is hereby corrected as shown below:

Column 1,
Line 8, insert the following paragraph:

-- ACKNOWLEDGMENT OF FEDERAL RESEARCH SUPPORT

This invention was made, at least in part, with funding from the United States Department of Energy under contract #DE-FG05-93ER61737. Accordingly, the United States Government may have certain rights in this invention. --

Signed and Sealed this

Fifteenth Day of February, 2005

JON W. DUDAS
*Director of the United States Patent and Trademark Office*